(12) United States Patent
Doi (10) Patent No.: US 6,864,247 B2
(45) Date of Patent: Mar. 8, 2005

(54) THERAPEUTIC AGENTS FOR GLOMERULOSCLEROSIS

(76) Inventor: Toshio Doi, 495-1-102, Kaikoji-cho, Motoseiganjisagaruhigashiiru, Aburanokojidori, Kyoto-shi, Kyoto 602-0946 (JP)

( * ) Notice: Subject to any disclaimer, the term of this patent is extended or adjusted under 35 U.S.C. 154(b) by 133 days.

(21) Appl. No.: 10/314,389

(22) Filed: Dec. 9, 2002

(65) Prior Publication Data

US 2003/0083320 A1 May 1, 2003

Related U.S. Application Data (63) Continuation of application No. 09/959,898, filed as application No. PCT/JP00/02958 on May 9, 2000, now Pat. No. 6,506,741.

(30) Foreign Application Priority Data

May 10, 1999 (JP) ............................................. 11-128566

(51) Int. Cl.$^7$ ............................................. A01N 45/00
(52) U.S. Cl. ........................ 514/168; 514/167; 514/739; 424/9.1
(58) Field of Search ............................... 514/167, 168, 514/739; 552/653; 424/1.11, 9.1

(56) References Cited

U.S. PATENT DOCUMENTS 6,506,741 B1 * 1/2003 Doi ............................ 514/167

FOREIGN PATENT DOCUMENTS

| JP | 9-110717 A | 4/1997 |
| JP | 9-169648 A | 6/1997 |
| JP | 02-028114 | 4/1998 |
| JP | 10-306024 A | 11/1998 |

OTHER PUBLICATIONS

English translation of abstract of JP 02–028114, 1998, p. 1.
Junko Abe, et al, "Prevention of Immunological Disorders in MRL/1 Mice by a New Synthetic Analogue of Vitamin $D_3$: 22–Oxa–1α,25–Dihydroxyvitamin $D_3$" J. Nutr. Sci. Vitaminol., vol. 36, 1990, pp. 21–31.
Yue J. Liu and Boon S. Ooi, "Responses of Mesangial Cells of Autoimmune Mice to Cyokines" Journal of Immunology, vol. 151, No. 4, Aug. 15, 1993, pp. 2247–2251.
Abe et al, "A Vitamin D Analog Regulates Mesangial Cell Smooth Muscle Phenotypes in a Transforming Growth Factor–Beta Type II Receptor–Mediated Manner, " *The Journal of Biological Chemistry*, vol. 274, No. 99, Jul. 23, 1999, pp. 20874–20878, United States.

* cited by examiner

*Primary Examiner*—Dameron L. Jones
(74) *Attorney, Agent, or Firm*—Browdy and Neimark, P.L.L.C.

(57) ABSTRACT

An object of the present invention is to provide pharmaceutical compositions for inhibiting mesangial cell proliferation or mesangial matrix production without causing hypercalcemia.

According to the present invention, therapeutic agents for glomerulosclerosis containing 1α,3β-dihydroxy-20α-(3-hydroxy-3-methylbutyloxy)-9,10-seco-5,7,10 (19)-pregnatriene as an active ingredient are provided.

3 Claims, 9 Drawing Sheets

Col I   Control

Fig. 5

Col I   Thy1

Fig. 6

Col I  Thy1+1,25(OH)₂D₃

Fig. 7

Col I  Thy1 + OCT

*Fig. 8*

Col IV  Control

*Fig. 9*

Col IV  Thy 1

Fig. 10

Col IV  Thy1+ 1,25(OH)$_2$D$_3$

Fig. 11

Col IV  Thy1+ OCT

FIG. 13

THERAPEUTIC AGENTS FOR GLOMERULOSCLEROSIS

This is a continuation of parent application Ser. No. 09/959,898, nationalized Nov. 13, 2001, now U.S. Pat. No. 6,506,741 of which the International application PCT/JP00/02958 was filed May 9, 2000, which designated the United States and which international application was not published in English, said co-pending parent application having now issued as U.S. patent 6,506,741.

TECHNICAL FIELD

The present invention relates to therapeutic agents for glomerulosclerosis containing 1α,3β-dihydroxy-20α-(3-hydroxy-3-methylbutyloxy)-9,10-seco-5,7,10 (19)-pregnatriene (hereinafter also referred to as 22-oxa-1α,25-dihydroxyvitamin $D_3$) as an active ingredient.

BACKGROUND ART

Glomerulosclerosis is induced by irreversible progress of various glomerular diseases of different etiologies and histopathological pictures. It is mainly pathologically characterized by mesangial cell proliferation or increased mesangial matrix accompanied by atrophy, degeneration or collapse of glomerular cells. Examples of the etiologies of glomerulosclerosis include IgA nephropathy or diabetic nephropathy, which were reported to be characterized by mesangial cell proliferation or increased mesangial matrix. In order to establish a therapy for glomerulosclerosis, it seems important to clarify the mechanism of the onset or to understand the pathology. Thus, efforts have been made to develop experimental nephritis models that experimentally induce lesions with mesangial cell proliferation and mesangial matrix production, and a rat model of anti-Thy 1 antibody-induced nephritis was prepared (Bagchus, W. M. et al., Lab. Invest, Vol. 55, No. 6, pp. 680–687, 1986). This model shows glomerular nephritis with mesangial cell proliferation and mesangial matrix production caused by the reaction between Thy 1 antigen existing as a membrane protein in mesangial cells and an antibody against it, and drug efficacy tests in this model were reported (Masashi Haraguchi et al., Kidney International, Vol. 51 (1997), pp. 1838–1846).

Drugs such as antitumor agents or immunosuppressive agents based on activated vitamins $D_3$ (i.e., 1,25-dihydroxyvitamins $D_3$) have been developed since they were reported to have not only a calcemic action but also a differentiation-inducing effect (Abe E. et al., Proc. Natl. Acad. Sci. USA, Vol. 78, No. 8, pp. 4990–4994, 1981). 1,25-Dihydroxyvitamins $D_3$ were also reported to have an antiproliferative effect on human mesangial cells (Weinreich T. et al., American Journal of Kidney Diseases, Vol. XVIII, No. 3, 1991, pp. 359–366). However, it was difficult to use 1,25-dihydroxyvitamins $D_3$ for antiproliferative purposes due to hypercalcemia.

Thus, vitamin $D_3$ derivatives with a low calcemic action were researched and some derivatives were developed. One of such vitamin $D_3$ derivatives is 22-oxa-1α,25-dihydroxyvitamin $D_3$, which was reported to show a differentiation-inducing effect without causing hypercalcemia (Abe J. et al., FEBS Lett., Vol. 226, No. 1, pp. 58–62, 1987). Japanese Patent No. 2854600 describes that 22-oxa-1α,25-dihydroxyvitamin $D_3$ inhibits urinary protein excretion so that it is useful as a therapeutic agent for glomerulonephritis.

However, nothing has been shown about the effect of 22-oxa-1α,25-dihydroxyvitamin $D_3$ on mesangial cell proliferation or mesangial matrix production.

DISCLOSURE OF THE INVENTION

An object of the present invention is to provide pharmaceutical compositions having the effect of inhibiting mesangial cell proliferation or mesangial matrix production with a low calcemic action.

As a result of careful studies to attain the above object, the inventor accomplished the present invention on the basis of the finding that 22-oxa-1α,25-dihydroxyvitamin $D_3$ inhibits mesangial cell proliferation without causing hypercalcemia and also inhibits the expression of collagen in a rat model of anti-Thy 1 antibody-induced nephritis.

Accordingly, the present invention provides therapeutic agents for glomerulosclerosis containing 1α,3β-dihydroxy-20α-(3-hydroxy-3-methylbutyloxy)-9,10-seco-5,7,10 (19)-pregnatriene as an active ingredient.

Therapeutic agents for glomerulosclerosis of the present invention can be used as pharmaceutical compositions for inhibiting mesangial cell proliferation or excessive mesangial matrix production.

Therapeutic agents for glomerulosclerosis of the present invention can also be used as pharmaceutical compositions for inhibiting the overexpression of collagen in the mesangium.

The present application claims priority based on Japanese Patent Application No. 128566/1999, the disclosure of which is entirely incorporated herein as reference.

THE MOST PREFERRED EMBODIMENTS OF THE INVENTION

The present invention will now be described more in detail only for illustrative but non-limitative purposes.

$1\alpha,3\beta$-Dihydroxy-$20\alpha$-(3-hydroxy-3-methylbutyloxy)-9,10-seco-5,7,10 (19)-pregnatriene (ie, 22-oxa-$1\alpha,25$-dihydroxyvitamin $D_3$ or OCT) used as an active ingredient in the present invention is a known compound that can be synthesized by the process described in JPA No. 267550/86, for example.

However, the compound that can be used as an active ingredient in the present invention is not limited to 22-oxa-$1\alpha,25$-dihydroxyvitamin $D_3$, and other vitamin $D_3$ derivatives having the effect of inhibiting mesangial cell proliferation or mesangial matrix production with a low calcemic action such as 16-enevitamin $D_3$ derivatives can also be used.

The "mesangial cell" and "mesangial matrix" are explained below.

The mesangium is a tissue supporting capillary loops in the glomerulus of the kidney and composed of mesangial cells and mesangial matrix. Mesangial cells are known to maintain the loop structure of the glomerulus as well as have a phagocytic function or the ability to regulate glomerular blood flow. Mesangial cells have angiotensin II receptors and produce platelet-activating factor, prostaglandin, type IV collagen, fibronectin, etc. The mesangial matrix is an extracellular matrix component that surrounds mesangial cells.

The pharmacological effect of 22-oxa-$1\alpha,25$-dihydroxyvitamin $D_3$ used as an active ingredient in the present invention can be evaluated on a rat model of a anti-Thy 1 antibody-induced nephritis characterized by showing increased mesangial cell proliferation and mesangial matrix production after administration of an anti-Thy 1 antibody. The pharmacological effect of test compounds can be evaluated by administering an anti-Thy 1 antibody to such a rat model followed by the test compounds, collecting renal tissue at an appropriate time and determining the glomerular cell count or glomerulosclerosis index or determining the expression of collagen by a standard method such as an immunohistochemical technique.

The mode of administration of pharmaceutical compositions of the present invention is not specifically limited, either oral or parenteral (for example, intravenous, intramuscular, intraperitoneal, etc.).

Pharmaceutical compositions of the present invention are preferably formulated and used in appropriate dosage forms including, but not limited to, tablets, granules, fine granules, capsules, powders, injections, solutions, suspensions, emulsions, transdermal patches and suppositories containing $1\alpha,3\beta$-dihydroxy-$20\alpha$-(3-hydroxy-3-methylbutyloxy)-9,10-seco-5,7,10 (19)-pregnatriene as an active ingredient optionally in combination with pharmaceutically acceptable carriers, excipients, disintegrators, lubricants, binders, perfumes, colorants, etc.

The dose can be appropriately chosen to be effective for inhibiting excessive mesangial cell proliferation or excessive mesangial matrix (e.g., collagen) production in the subject depending on the disease to be treated, the condition, body type, constitution, age and sex of the patient, and the administration route, dosage form or other factors. The dose expressed in the weight of an active ingredient is typically in the range of 0.001–1000 $\mu$g/kg/day, preferably 0.01–100 $\mu$g/kg/day, more preferably 0.1–10 $\mu$g/kg/day.

The following example further illustrates the present invention without, however, limiting the same thereto.

EXAMPLE 1

Test Method

A rat model of anti-Thy 1 antibody-induced nephritis was prepared, which showed increased mesangial cell proliferation and mesangial matrix production on days 4–7 after antibody administration. An anti-Thy 1 antibody (OX-7 purchased from CEDARLANE, Ontario, Canada) was administered into the tail vein of 6-week-old male Wistar rats at 1 mg/kg to induce anti-Thy 1 nephritis. Next day after OX-7 administration, 22-oxa-$1\alpha,25$-dihydroxyvitamin $D_3$ was intravenously administered at 0.4 $\mu$g/kg every two days, and on day 7 after administration, serum, urine and renal tissue were collected.

For comparison, $1\alpha,25$-dihydroxyvitamin $D_3$ was administered in the same manner instead of 22-oxa-$1\alpha,25$-dihydroxyvitamin $D_3$. Rats not treated with the anti-Thy 1 antibody were used as normal controls. Rats treated with the anti-Thy 1 antibody alone without any vitamin D derivative were used as disease controls.

Figure 1:
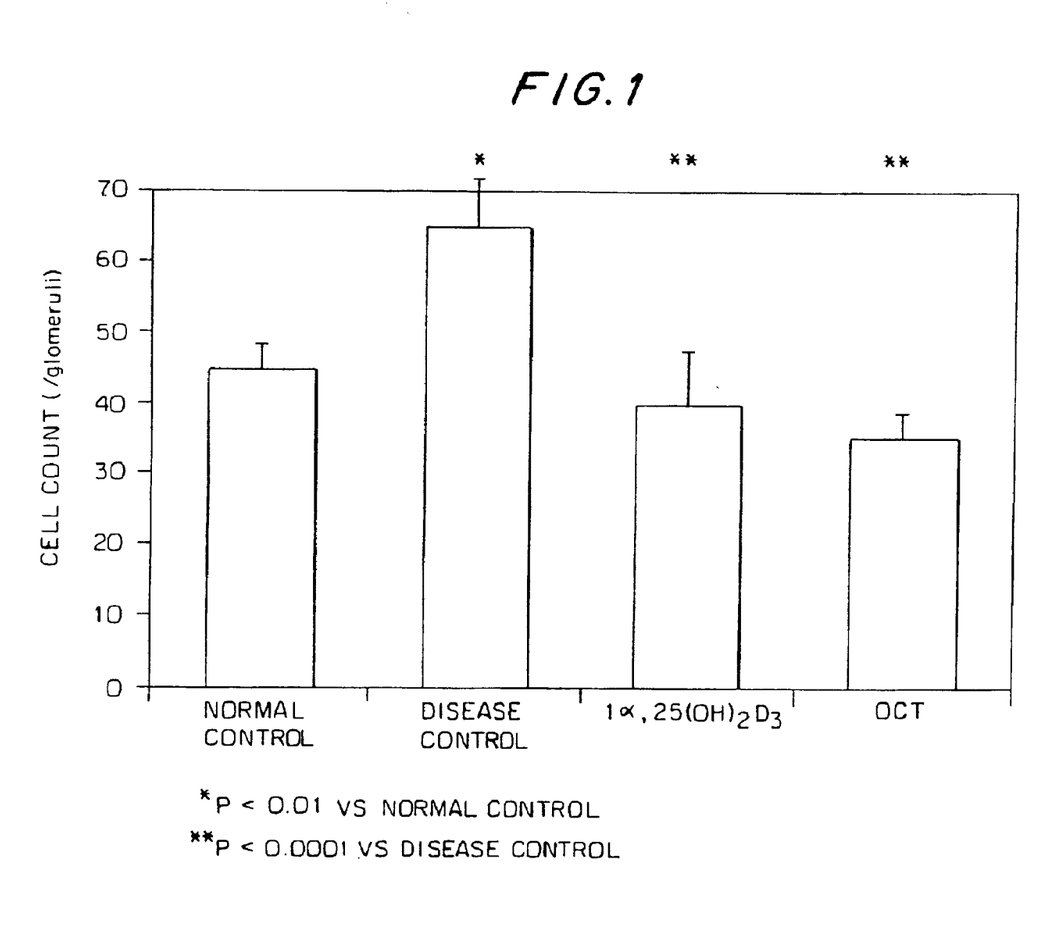
FIG. 1 is a graph showing changes in glomerular cell count in a rat model treated with vitamin D derivatives. In this and the subsequent figures, "OCT" represents a group treated with an anti-Thy 1 antibody and 22-oxa-1α,25-dihydroxyvitamin $D_3$, "1α,25-dihydroxyvitamin $D_3$" represents a group treated with the anti-Thy 1 antibody and 1α,25-dihydroxyvitamin $D_3$, "Disease control" represents a group treated with the anti-Thy 1 antibody alone, and "Normal control" represents an untreated group.
Figure 2:
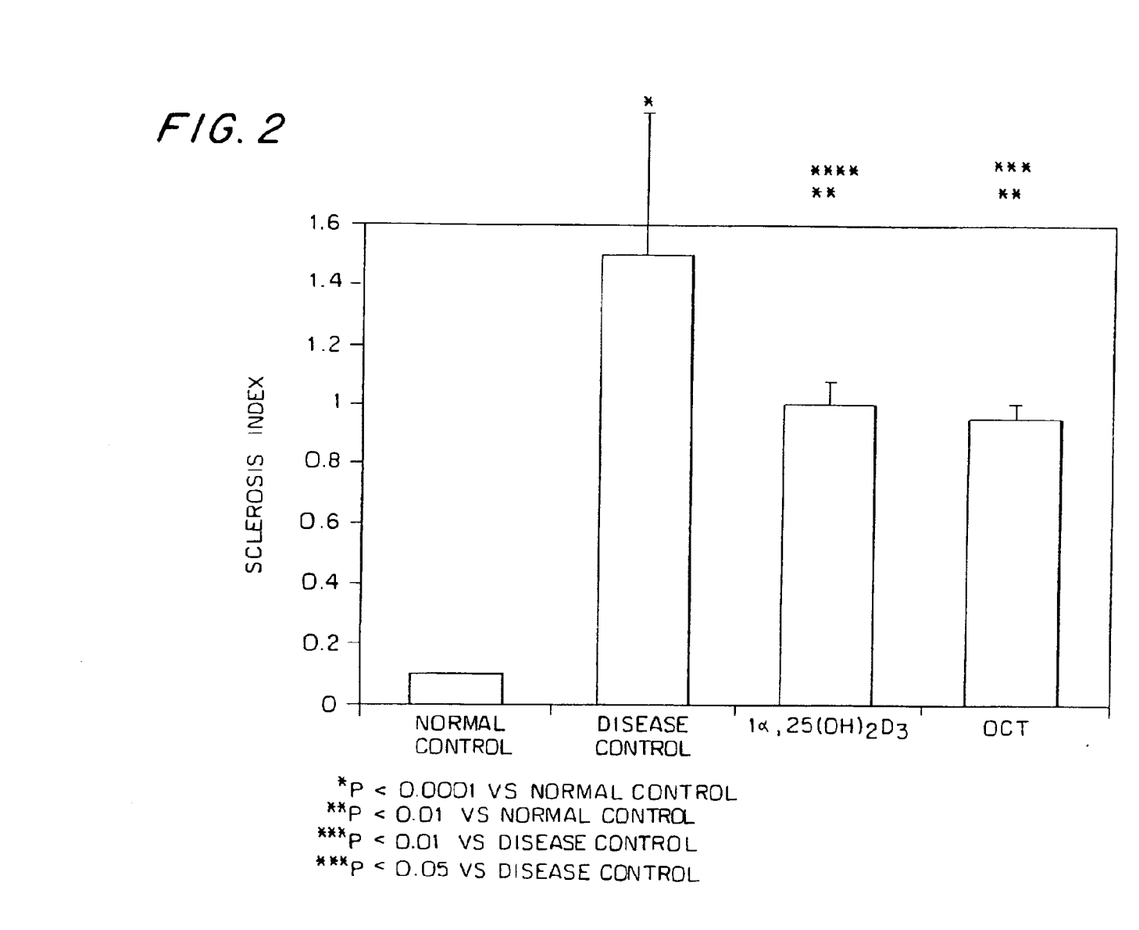
FIG. 2 is a graph showing changes in glomerulosclerosis index in the rat model treated with vitamin D derivatives.
Figure 3:
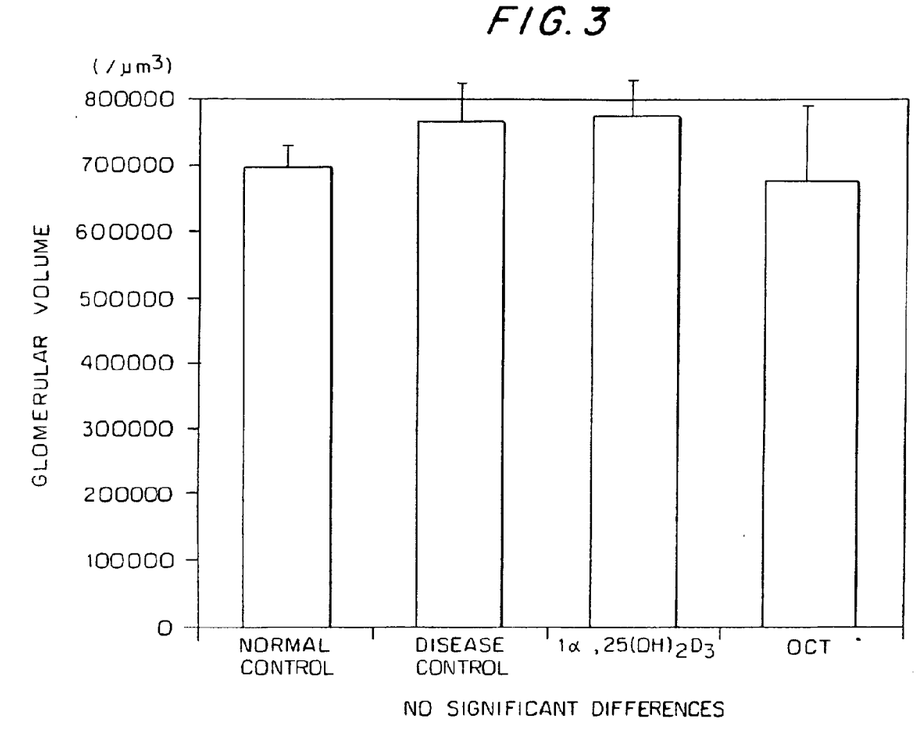
FIG. 3 is a graph showing changes in glomerular volume in the rat model treated with vitamin D derivatives.
Figure 4:
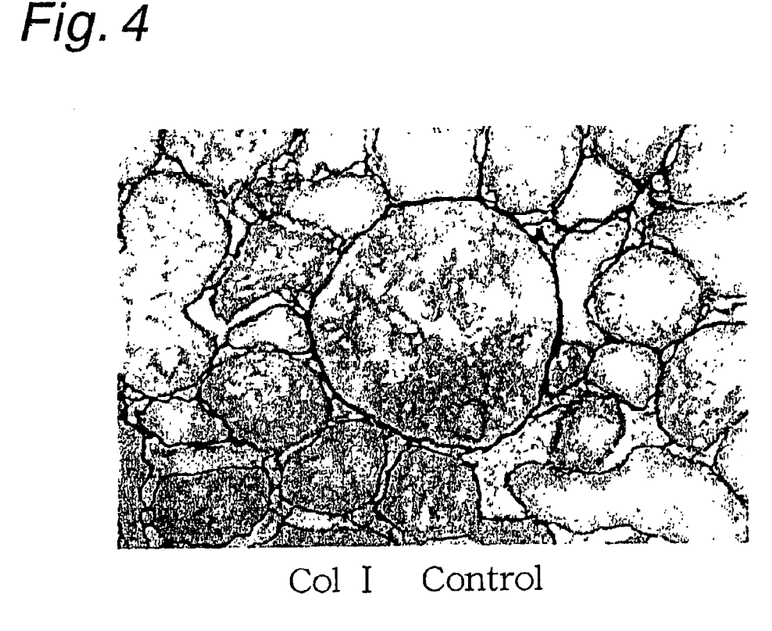
FIG. 4 shows immunohistochemical results of type I collagen expression in the control rat model.
Figure 5:
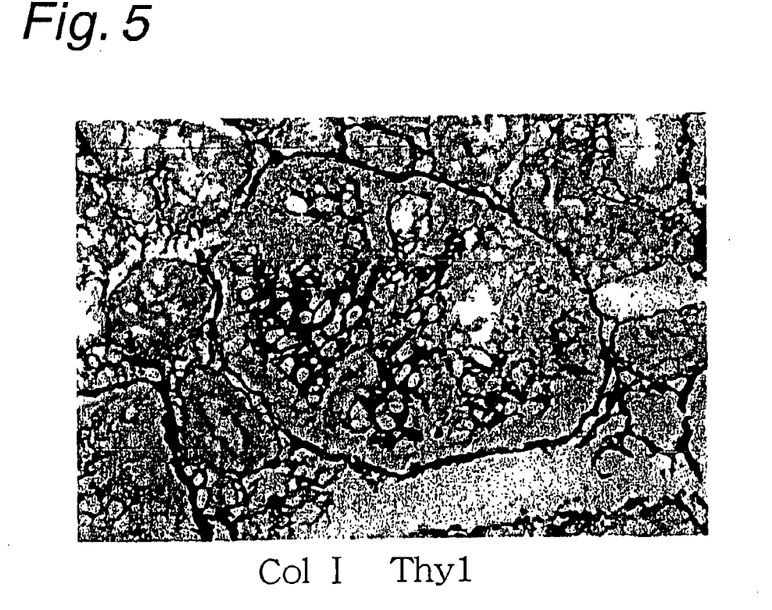
FIG. 5 shows immunohistochemical results of type I collagen expression in the rat model treated with the anti-Thy 1 antibody.
Figure 6:
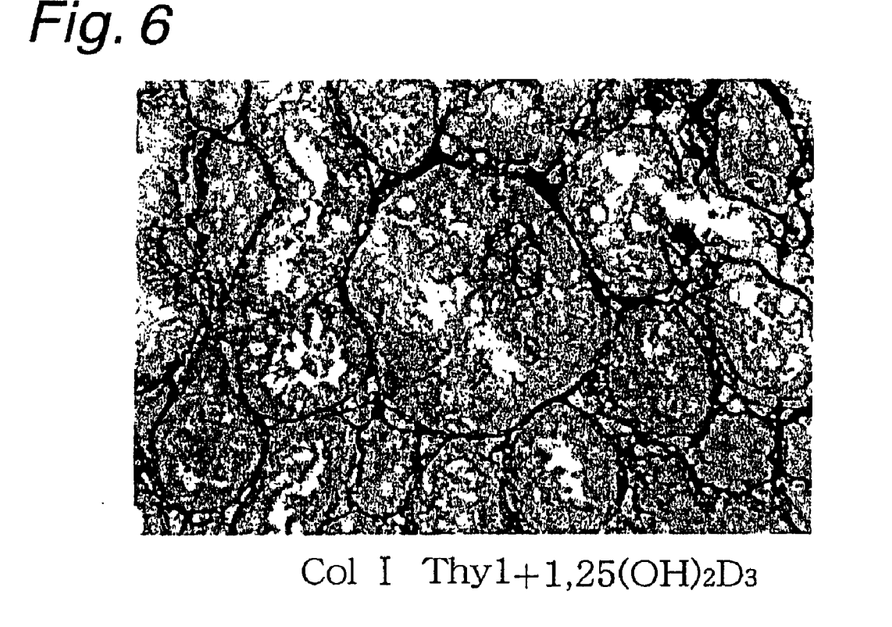
FIG. 6 shows immunohistochemical results of type I collagen expression in the rat model treated with the anti-Thy 1 antibody and 1α,25-dihydroxyvitamin $D_3$.
Figure 7:
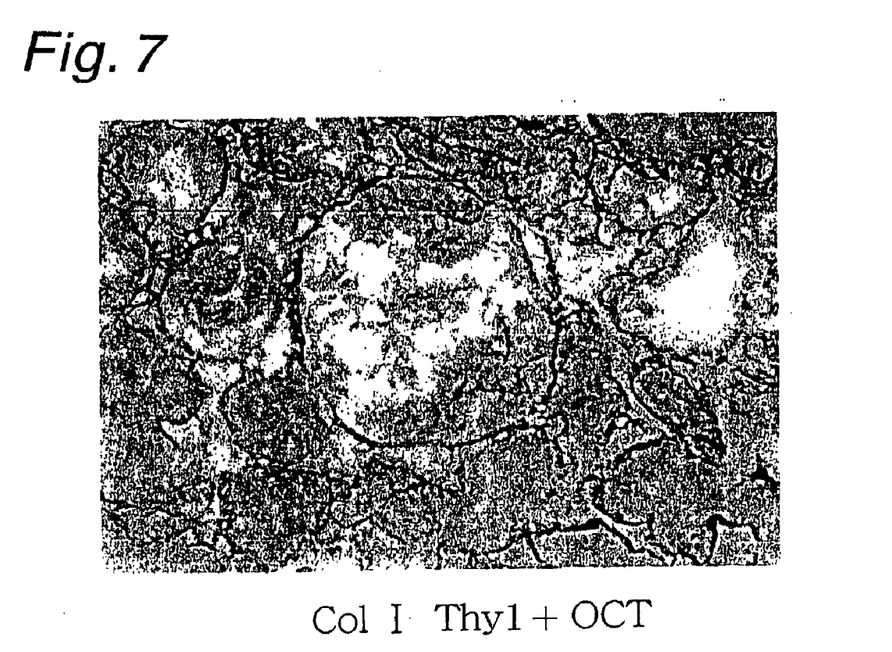
FIG. 7 shows immunohistochemical results of type I collagen expression in the rat model treated with the anti-Thy 1 antibody and 22-oxa-1α,25-dihydroxyvitamin $D_3$.
Figure 8:
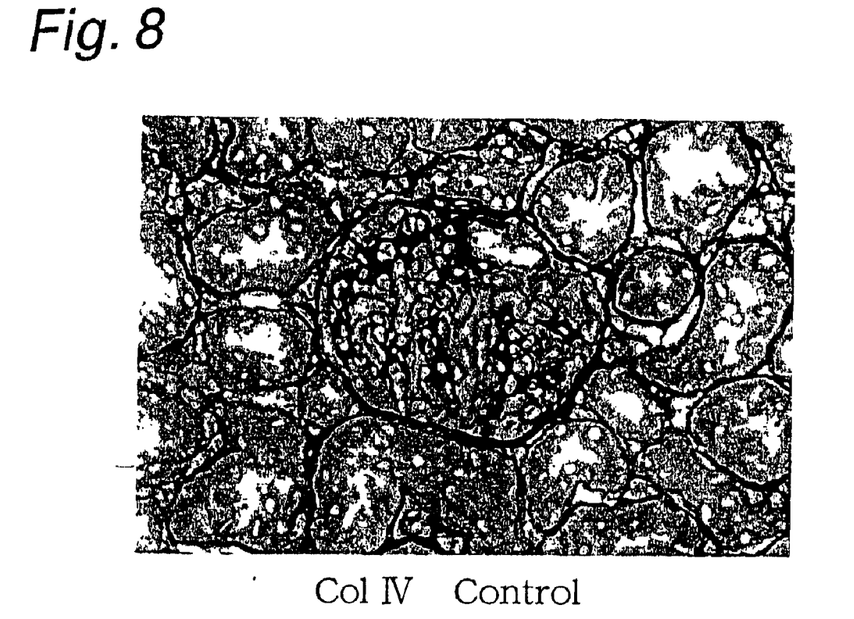
FIG. 8 shows immunohistochemical results of type IV collagen expression in the control rat model.
Figure 9:
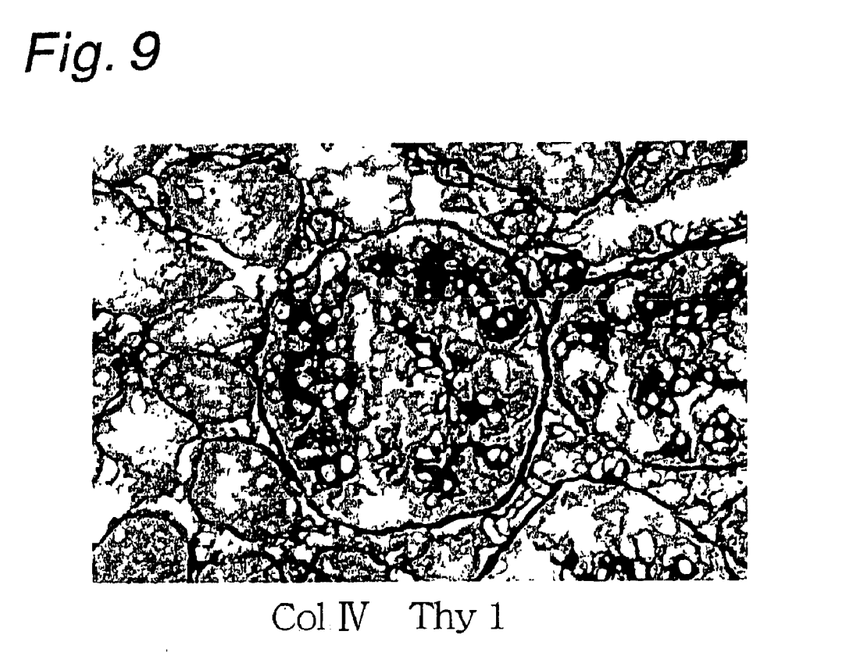
FIG. 9 shows immunohistochemical results of type IV collagen expression in the rat model treated with the anti-Thy 1 antibody.
Figure 10:
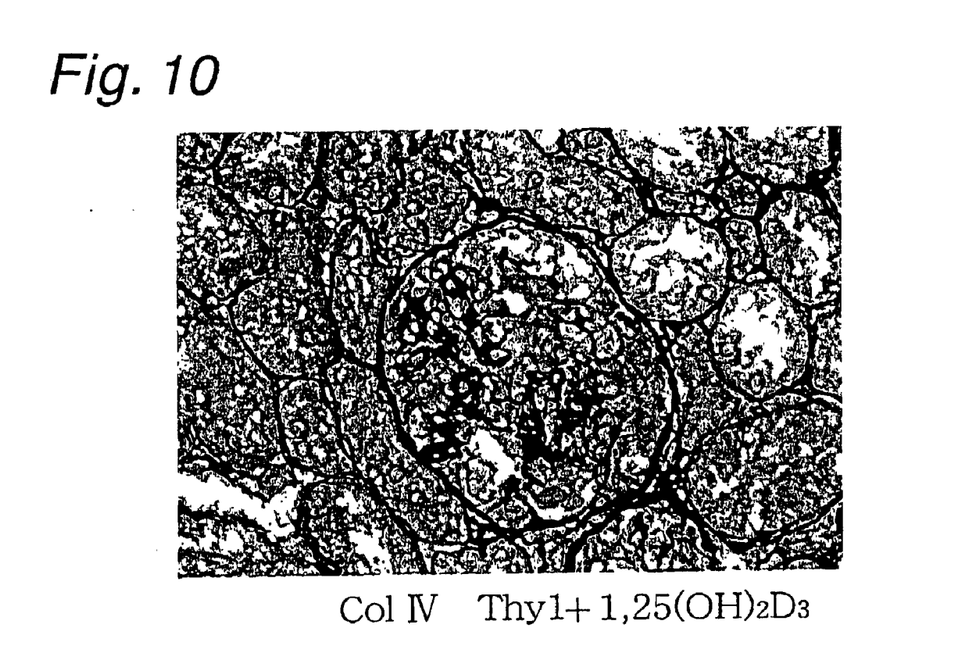
FIG. 10 shows immunohistochemical results of type IV collagen expression in the rat model treated with the anti-Thy 1 antibody and 1α,25-dihydroxyvitamin $D_3$.
Figure 11:
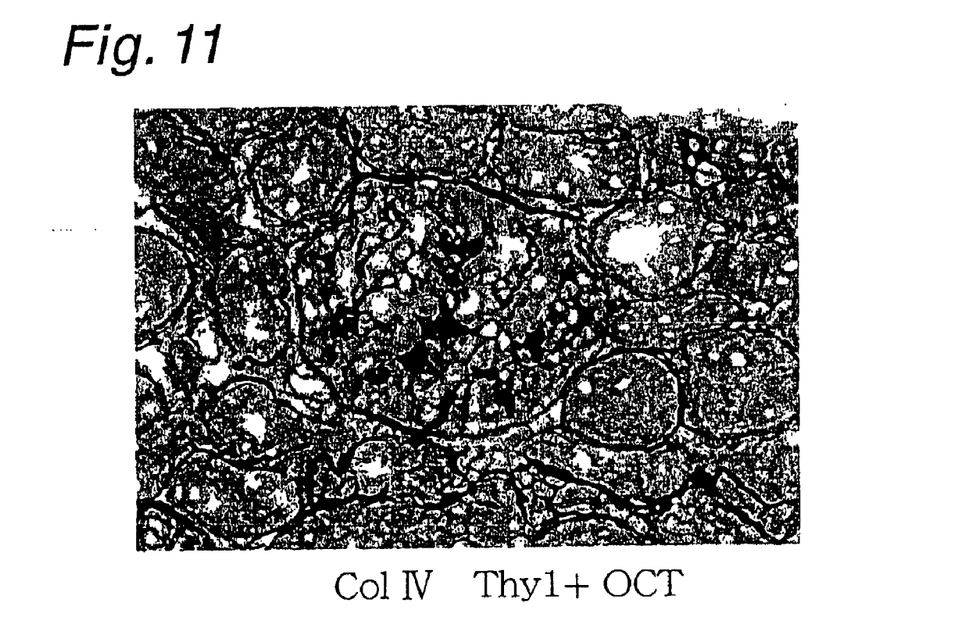
FIG. 11 shows immunohistochemical results of type IV collagen expression in the rat model treated with the anti-Thy 1 antibody and 22-oxa-1α,25-dihydroxyvitamin $D_3$.

In the renal tissue, the glomerular cell count, glomerulosclerosis index and glomerular volume were determined (FIGS. 1, 2 and 3). The "glomerular cell count" was determined by counting every cell in every measurable glomerulus on hematoxylin-eosin stained samples. The "glomerulosclerosis index" was evaluated on PAM (periodic acid-methenamine-silver) stained samples according to the method of Raji et al. The "glomerular volume" was determined by using NIH image to calculate the volume of glomeruli read by an image analyzer.

In the renal tissue, the expression of type I collagen (ColI) and type IV collagen (ColIV) in the mesangium was immunohistologically examined (FIGS. 4–11). Staining was performed on 4 $\mu$m sections using an ABC Elite peroxidase staining kit (Vector Lab., Burlingame, Calif., U.S.A.) according to the manufacturer's instructions. The primary antibodies used were a guinea pig anti-rat type I collagen antibody (Boehringer Ingelheim, Co., Ltd., Ingelheim, Germany) and a rabbit anti-rat type IV collagen antibody (Boehringer Ingelheim, Co., Ltd., Ingelheim, Germany).

Figure 12:
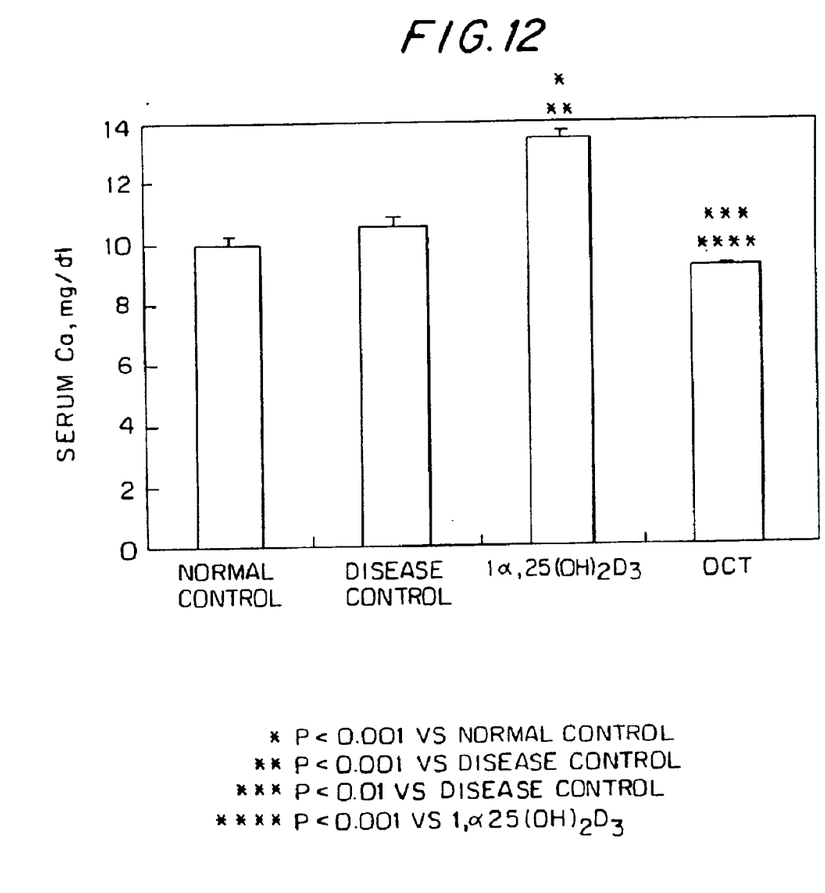
FIG. 12 is a graph showing changes in serum calcium (Ca) in the rat model treated with vitamin D derivatives.
Figure 13:
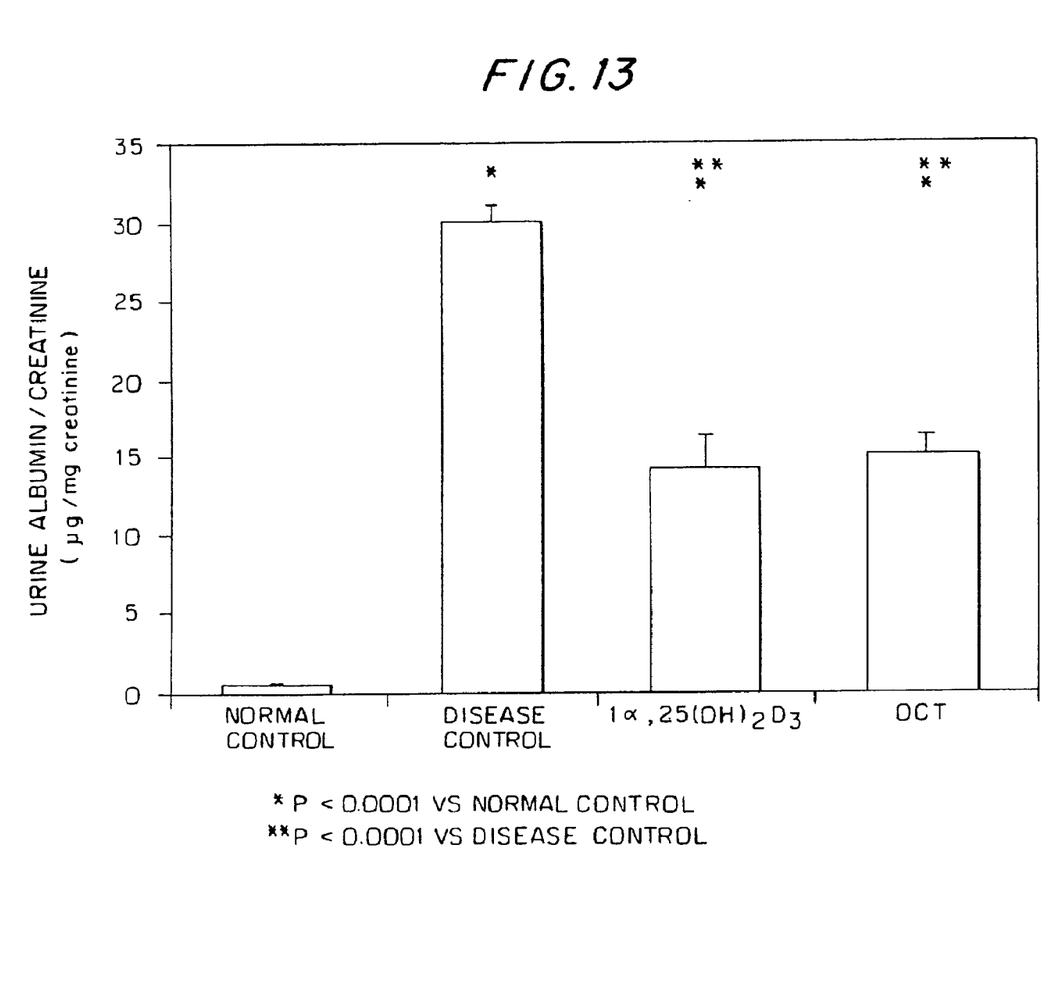
FIG. 13 is a graph showing changes in urinary albumin (uALB) in the rat model treated with vitamin D derivatives.

In addition, serum calcium (Ca) was determined with an autoanalyzer (AUTOANALYZER, HITACHI 7170, Tokyo, Japan) and urinary albumin (uALB) was determined with an ELISA kit NEPHRAT II (EXOCELL, INC) (FIGS. 12 and 13).

Results (1) Glomerular Cell Count, Glomerulosclerosis Index and Glomerular Volume Administration of $1\alpha,25$-dihydroxyvitamin $D_3$ and 22-oxa-$1\alpha,25$-dihydroxyvitamin $D_3$ significantly suppressed glomerular cell count (FIG. 1) and glomerulosclerosis index (FIG. 2) but showed no effect on glomerular volume (FIG. 3).

(2) Immunohistochemical Analysis (ColI, ColIV)

FIGS. 4–8 and 9–11 show that administration of $1\alpha,25$-dihydroxyvitamin D3 and 22-oxa-$1\alpha,25$-dihydroxyvitamin $D_3$ clearly inhibited the expression of ColI and ColIV.

(3) Ca and uALB Levels

Administration of 22-oxa-1α,25-dihydroxyvitamin $D_3$ significantly suppressed uALB levels without increasing serum Ca levels. However, administration of 1α,25-dihydroxyvitamin $D_3$ showed a significant increase in serum Ca levels though uALB levels were significantly suppressed (FIGS. 12 and 13).

INDUSTRIAL APPLICABILITY

As described above, it was shown that 22-oxa-1α,25-dihydroxyvitamin $D_3$ inhibits mesangial cell proliferation and excessive mesangial matrix production in a rat model of anti-Thy 1 nephritis without increasing serum calcium, thereby inhibiting the progress of glomerulosclerosis. Therefore, the present compound is useful as a therapeutic agent for inhibiting the progress of glomerulosclerosis without inducing hypercalcemia.

What is claimed is:

1. A method of treating diabetic nephropathy, comprising administering to a host in need of such a treatment a therapeutically effective amount of 1α,3β-dihydroxy-20α-(3-hydroxy-3-methylbutyloxy)-9,10-seco-5,7,10(19)-pregnatriene.

2. The method of claim 1, wherein said host is a patient in need of inhibition of mesangial cell proliferation or mesangial matrix production.

3. The method of claim 1, in which said host is a patient in need of inhibition of expression of collagen in the mesangium.

* * * * *

UNITED STATES PATENT AND TRADEMARK OFFICE
CERTIFICATE OF CORRECTION

PATENT NO. : 6,864,247 B2  Page 1 of 1
APPLICATION NO. : 10/314389
DATED : March 8, 2005
INVENTOR(S) : Doi et al.

It is certified that error appears in the above-identified patent and that said Letters Patent is hereby corrected as shown below:

On the cover page, item (*), below the Notice insert --This patent is subject to a terminal disclaimer. --

Signed and Sealed this

Sixth Day of November, 2007

JON W. DUDAS
*Director of the United States Patent and Trademark Office*